(12) United States Patent
Verhaegen

(10) Patent No.: US 6,380,605 B1
(45) Date of Patent: *Apr. 30, 2002

(54) DEVICE AND A METHOD FOR THERMAL SENSING

(75) Inventor: Katarina Verhaegen, Leuven (BE)

(73) Assignee: IMEC vzw, Leuven (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,176

(22) Filed: Dec. 19, 1997

(51) Int. Cl.$^7$ ................................................ H01L 31/058
(52) U.S. Cl. ........................ 257/467; 136/224; 136/231; 374/13
(58) Field of Search ................................. 257/467, 468, 257/469, 470; 136/208, 209, 210, 211, 212, 224, 225, 226, 227, 230, 231, 232, 233; 374/10, 11, 12, 13

(56) References Cited

U.S. PATENT DOCUMENTS

| | | | |
|---|---|---|---|
| 5,813,764 A | * | 9/1998 | Visser et al. ................... 374/12 |
| 6,079,873 A | * | 6/2000 | Cavicchi et al. ............... 374/10 |

FOREIGN PATENT DOCUMENTS

| FR | 1 411 251 A | 12/1965 |
|---|---|---|
| JP | 4-372865 | * 12/1992 |

OTHER PUBLICATIONS

Design of a High–Throughput Microphysiometer, Katarina Verhaegen, et al., Sep. 30, 1998.
Abstract forming basis of a Poster Presentation entitled "A High Throughput Microfysiometer" presented Sep. 30, 1996—Oct. 1, 1996 in Oxford England.
Van Gerwen, P., et al., "Thin–Film boron–doped polycrystalline silicon$_{70}$–Germanium$_{30}$for thermopiles", vol. A53, May 1996.
Köhler, et al., "Microanalytical estimation of cerium by a miniaturized thermoelectrical sensor", vol. B23, No. 1, Jan. 1995.

* cited by examiner

Primary Examiner—Sara Crane
(74) Attorney, Agent, or Firm—Knobbe, Martens, Olson & Bear, LLP

(57) ABSTRACT

A device for thermal sensing is disclosed based on only one thermopile. The cold junctions of said thermopile are coupled thermally to a first channel comprising a first substance while the hot junctions of said thermopile are coupled thermally to a second channel comprising a second substance, said first and said second channel are separated and thermally isolated one from another. Said device can further comprise a membrane to thermally and electrically isolate said thermopile and to mechanically support said thermopile. Particularly a liquid rubber, i.e. ELASTOSIL LR3003/10A, B can be used as a membrane material. Further disclosed is a method for fabricating such a device using micromachining techniques.

6 Claims, 4 Drawing Sheets a)

b)

c)

d)

a)

b)

c)

d)

e)

f)

DEVICE AND A METHOD FOR THERMAL SENSING

FIELD OF THE INVENTION

The present invention is related to a device which yields an electrical output signal but has an input or intermediate signal of the thermal type. Such a device can be used to characterize chemical and physical processes which are accompanied by changes in heat content or enthalpy. Furthermore a method is disclosed for manufacturing said device by means of micromachining which is a technique closely related to the technique used for the manufacturing of integrated circuits.

BACKGROUND OF THE INVENTION

New approaches in the combinatorial chemistry have resulted in the capability of producing millions of compounds in a short time. Analysis of each compound with respect to multiple parameters is proving to be a significant bottleneck as in e.g. M. A. Shoffner et al., Nucleic Acids Research, 1996, vol. 24, No. 2, pp. 375–9. The number of cells, the test reagent volumes, the throughput rate and the ease of use through automation are all important parameters which should be optimized in order to meet the stringent requirements for modern drug screening. Furthermore a small amount of precious reagent reduces both cost and waste, and increases the number of possible analyses. A candidate for this kind of analysis is a calorimeter. A calorimeter is a device which yields an electrical output signal but has an input or intermediate signal of the thermal type. Calorimetry, more than pH-metry, offers the advantage of generality: all chemical and physical processes are accompanied by changes in heat content, or enthalpy. In fact microcalorimeters can be used for the analysis of the activity of biological cells, chemical reactions in small volumes and other microanalytical applications.

The most frequently used commercially available calorimeters are the Thermometric 2277 Thermal Activity Monitor and the MicroCal MCS Isothermal Titration Calorimeter. They are both based on the use of two or more thermoelectric devices, so called thermopiles, having a common heat sink as reference. A thermopile is at least one thermocouple which is a temperature sensing element and which is connected to identical thermocouples in parallel thermally and in series electrically. Thermocouples do not measure the temperature itself, but rather the temperature difference between two junctions. An advantage of using thermocouples as temperature sensing elements is that there is no offset, i.e. when there is no temperature difference there is no voltage, which makes calibration superfluous. A thermocouple as illustrated in FIG. 2, i.e. a combination of two different (semi)conductive materials, converts a thermal difference between its two junctions into a voltage difference by means of the combined Seebeck coefficient S of its two structural thermo-electric materials. In fact a thermocouple comprises a first conductive material (14) and a second conductive material (13) with an insulating layer (15) inbetween. A thermocouple has a so-called hot junction (11), where said first material and said second material are short-circuited, and a so-called cold junction (15), where said first and said second material are separated one from another by means of said insulating layer. At said cold junction the electrical output signal, representing the temperature difference $\Delta T$ between said hot junction and said cold junction, can be measured.

The total generated voltage is the sum of the thermocouple voltages. For n (n being a positive whole number greater than zero) thermocouples, where each thermocouple is identical, it can be written that:

$$U_{tp} = n * S * \Delta T.$$

The temperature difference $\Delta T$ is the product of the generated power difference between the two junction sites and the thermal resistance:

$$\Delta T = \Delta P_{gen} * R_{th}$$

Thermopiles are preferred because they are self-generating, easy to integrate and because the temperature changes involved are low frequency signals.

The drawbacks of these state-of-the art devices are the following. These devices have at least two thermopiles and a common heat sink. The cold junctions of each thermopile are thermally coupled to the common heat sink which is at a known temperature. The hot junctions of each thermopile are thermally coupled to a substance under test. So in fact, one tries to perform a kind of absolute measurement by measuring the temperature difference between this substance under test and the heat sink at known temperature. By applying different substances under test to different thermopiles as e.g. for drug screening where the hot junctions of a first thermopile are coupled to reference cells and the hot junctions of a second thermopile are coupled to genetically engineered cells expressing a drug target. When the potential drug candidate is effective, it will activate the genetically engineered cells which results in a heat change. This heat change is determined indirectly by subtracting the measured signals of the first and the second thermopile, where the cold junctions of both thermopiles are coupled to a common heat sink at known temperature. This is a cumbersome approach which lacks accuracy and demands a space consuming design.

SUMMARY OF THE INVENTION

In an aspect of the invention a device is disclosed based on only one thermopile wherein said thermopile is in contact with at least parts of a substrate, e.g. a silicon wafer or the remains thereof. The cold junctions of said thermopile are coupled thermally to a first channel comprising a first substance while the hot junctions of said thermopile are coupled thermally to a second channel comprising a second substance, said first and said second channel are separated and thermally isolated one from another. Said device is capable of handling a very small amount of a substance, typically in the range from 1 microliter to 30 microliter.

In an aspect of the invention a device for monitoring chemical and physical processes which are accompanied by changes in heat content or enthalpy is disclosed, comprising a thermopile, wherein said thermopile is in contact with at least parts of a substrate, e.g. a silicon wafer or the remains thereof, and wherein said thermopile is a set of at least one thermocouple comprising a first conductive material and a second conductive material with an insulating layer inbetween. Said first and said second material are chosen such that their thermo-electric voltages are different. A first substance, i.e. a reference substance, can be thermally coupled to the cold junctions of said thermopile while a second substance, i.e. a test substance, can be thermally coupled to the hot junctions of the same thermopile. Alternatively, a first substance, i.e. a test substance, can be thermally coupled to the cold junctions of said thermopile while a second substance, i.e. a reference substance, can be thermally coupled to the hot junctions of the same thermopile. To speed up measurement time or to test a number of substances at the same time, a modular system comprising an array of devices, each device comprising one thermopile, can be configured on the same substrate. Said device can further comprise a thin insulating layer, e.g. an oxide layer or a nitride layer, on said thermopile in order to prevent a direct contact between the substances and the thermopile to thereby avoid damaging said thermopile. Said device further comprises a membrane to thermally and electrically isolate said thermopile and to mechanically support said thermopile. Silicon oxide and/or silicon nitride can be used as membrane materials. Particularly a liquid rubber, i.e. ELASTOSIL LR3003/10A, B can be used as a membrane material.

In an aspect of the invention a method is disclosed for fabricating a device used to monitor chemical and physical processes which are accompanied by changes in heat content or enthalpy. The device is capable of handling a very small amount of a substance. These requirements can be achieved by micromachining, a technique closely related to integrated circuit fabrication technology. The starting material is a substrate like e.g. a semiconductive wafer, particularly a monocrystalline silicon wafer, or a slice of an insulating material, i.e. a glass slice. On this substrate layers can be coated, patterned by means of a sequence of lithographic steps and wet and/or dry etching steps. Such processed substrates can be bonded to each other or to other materials in order to make three-dimensional structures.

According to the invention a method is disclosed for fabricating rubber membranes. This method comprises the following steps:

On a first side of a substrate a silicon oxide/silicon nitride stack is deposited which will serve as an etch mask to define the membrane pattern. Other materials and/or other thickness and or another number of layers may be used to serve as an etch mask. Said substrate can be a semiconductive wafer or slice, like e.g. a silicon wafer, or an insulating slice like e.g. a glass slice.

On the second side of the substrate a silicon oxide/silicon nitride stack is deposited which will serve as an etch stop to define the membrane pattern. Other, preferably insulating, materials and/or other thickness and or another number of layers may be used to serve as an etch stop. One can also choose to omit this etch stop dependent on the etch procedure.

The etch mask on said first side of the substrate is patterned by means of a sequence of photolithographic steps and wet and/or dry etching steps.

The second side of the substrate is coated with liquid rubber, i.e. ELASTOSIL LR3003/10A, B. The relatively low viscosity of said rubber allows for a spin-coating technique. The surface of the substrate is chemically modified to make it water repellent by treating said surface with hexamethyldisiloxane (HMDS).

A second substrate is bonded onto the first by means of the unvulcanised rubber. The bonding is performed in low vacuum and the rubber is cured. Alternatively, instead of a second wafer a glass plate is used. A first side of this glass plate comprises a wax layer to protect the rubber layer of the first substrate because said first side is exposed to the rubber during the bonding process.

To free the membrane a chemical back etch is performed in KOH.

In an aspect of the invention a method is disclosed for fabricating a device used to monitor chemical and physical processes which are accompanied by changes in heat content or enthalpy. This method or process comprises the following steps:

On a first side of a substrate at least one hard mask layer is deposited which will serve as an etch mask for removing at least parts of said substrate.

On the second side of the substrate at least one hard mask layer can be deposited which can serve as an etch stop layer dependent on the etch procedure used and/or as an insulating layer to thermally and electrically isolate a thermopile and/or to inhibit a direct contact between a substance and said thermopile.

On said second side of the substrate a first conductive layer with a thickness typically in the range from 0.3 $\mu$m to 1 $\mu$m is deposited. Said first conductive layer, e.g. a doped polysilicon layer, is patterned to thereby form the first material of the thermopile, i.e. a set of thermocouples which are connected in parallel thermally and in series electrically.

On said first side of the substrate said hard mask layer is patterned in order to define the etch windows for etching away the underlying silicon in order to expose at least parts of the underlying thermopile or the etch stop multi-layer structure on said thermopile.

On said second side of the substrate an insulating layer is deposited with a thickness in the range typically from 0.2 $\mu$m to 1 $\mu$m or from 0.5 $\mu$m to 5 $\mu$m. Said insulating layer is used as an interconductive layer dielectric and isolates the different fingers of the pattern of the first conductive layer from each other. Said insulating layer is patterned to thereby form via holes through which the underlying first conductive layer can be contacted in order to form hot junctions.

A second conductive layer, having a thermo-electric voltage different from the thermoelectric voltage of said first conductive layer, i.e. an aluminum layer with a thickness of 200 nm, is deposited on said second side of the substrate. Said second conductive layer is patterned to thereby form the second material of the thermopile.

On said second side of the substrate an insulating layer is deposited to serve as a membrane. Said membrane should thermally and electrically isolate said thermopile and mechanically support said thermopile. Silicon oxide and/or silicon nitride can be used as membrane materials, but preferably a liquid rubber, i.e. ELASTOSIL LR3003/10A, B is used.

A second substrate can be bonded or glued onto said first substrate.

To expose the thermopile and the membrane, a chemical back etch is performed. Said back etch can be a sequence of etching steps using KOH as an etchant and wherein each etching step is performed with a weight percentage of KOH in the range from 20 to 60 percent and at a temperature in the range from 20 to 100° C. Alternatively an etch mask, e.g. a silicon oxide/silicon nitride stack, can be deposited and patterned on the free surface of said second substrate. By doing so, during the back etch e.g. only the glass or silicon underneath the thermopile is removed to thereby free the membrane.

DETAILED DESCRIPTION OF THE INVENTION

In relation to the appended drawings the present invention is described in detail in the sequel. Several embodiments are disclosed. It is apparent however that a person skilled in the art can imagine several other equivalent embodiments or other ways of practicing the present invention, the spirit and scope thereof being limited only by the terms of the appended claims.

A device is disclosed yielding an electrical output signal but having an input or intermediate signal of the thermal type. Said device can be used e.g. for the analysis of the activity of biological cells, chemical reactions in small volumes and other microanalytical applications. Particularly said device can be used to monitor chemical and physical processes which are accompanied by changes in heat content or enthalpy. Furthermore said device can be used to thermodynamically characterize a biological interaction as a means to rational drug design, to drug stability and drug effect studies on cells and blood.

Figure 1:
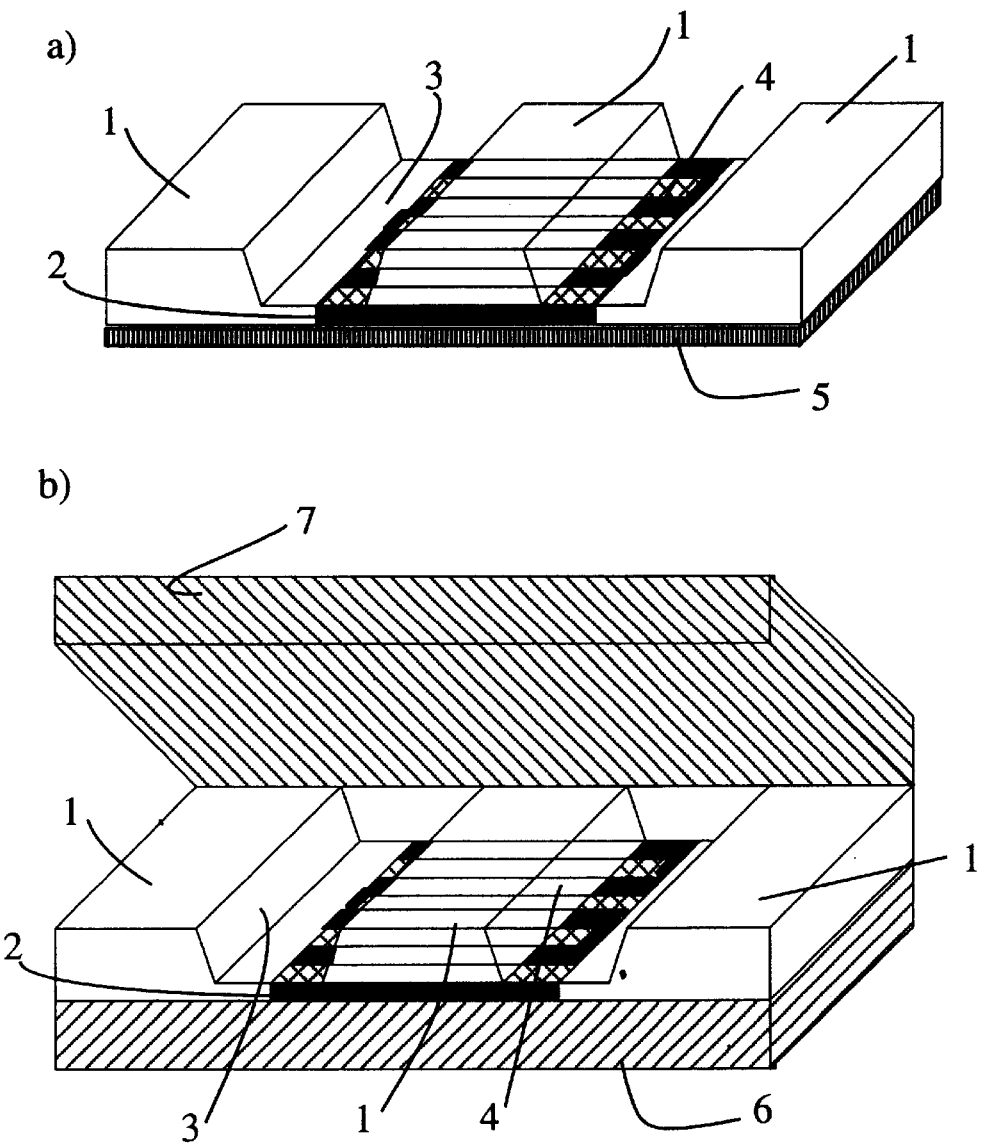
FIG. 1 depicts two schematic representations of a thermal sensing device according to two different embodiments of the present invention.
Figure 2:
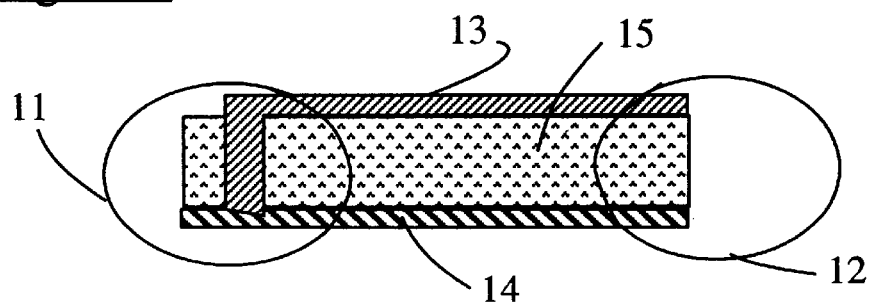
FIG. 2 depicts a schematic representation of a thermocouple, said thermocouple being part of a thermopile.

In an embodiment of the invention a device, as in FIG. 1, for monitoring chemical and physical processes which are accompanied by changes in heat content or enthalpy is disclosed, comprising a thermopile (2), wherein said thermopile is in contact with a part of a substrate (1), e.g. a silicon wafer or the remains thereof, and wherein said thermopile is at least one thermocouple (FIG. 2) comprising a first conductive material (14) and a second conductive material (13) with an insulating layer (15) inbetween. Said first and said second material are chosen such that their thermo-electric voltages are different. The choice of said conductive materials is further based on several parameters as there are the magnitude of their Seebeck coefficient, their electrical resistivity, their availability and their compatibility with standard processing steps as used in the manufacturing of integrated circuits. An increase in Seebeck coefficient corresponds with an increase in sensitivity while a lower resistivity corresponds with a lower noise level and thus an improved signal to noise ratio. Each thermocouple has a so-called hot junction (11), where said first material and said second material are short-circuited, and a so-called cold junction (12), where said first and said second material are separated one from another by means of said insulating layer. At said cold junction the electrical output signal, representing the temperature difference between said hot junction and said cold junction of the same thermopile, can be measured. Preferably said thermocouples of said thermopile are connected in parallel thermally and in series electrically. By doing so, the hot junctions as well as the cold junctions of the different thermocouples of the same thermopile are grouped.

A first substance, i.e. a reference substance, can be thermally coupled to the cold junctions of said thermopile while a second substance, i.e. a test substance, can be thermally coupled to the hot junctions of the same thermopile. Alternatively, a first substance, i.e. a test substance, can be thermally coupled to the cold junctions of said thermopile while a second substance, i.e. a reference substance, can be thermally coupled to the hot junctions of the same thermopile. Said first substance and said second substance can be brought in direct contact with said cold junctions and said hot junctions respectively using supply means, whereby said first substance is isolated from said second substance. Alternatively, said device can further comprise a first and a second channel on said thermopile, a first channel (3) in close vicinity of the cold junctions and a second channel (4) in close vicinity of the hot junctions, said first channel and said second channel being separated and isolated one from another. Said channels can be used to supply the substances, e.g. solutions, to said junctions. Furthermore said channels can also serve as molds for fitting in replaceable tubes, particularly replaceable glass tubes, wherein said tubes are used as supply means. Said tubes have a diameter typically in the micrometer range and can be made by micromachining techniques or can be readily bought.

Said device can further comprise a thin insulating layer, e.g. an oxide layer or a nitride layer, on said thermopile in order to prevent a direct contact between the substances and the thermopile to thereby avoid damaging said thermopile.

Said device further comprises a membrane (5) to isolate and mechanically support said thermopile. Said membrane should thermally and electrically isolate said thermopile and mechanically support said thermopile. Silicon oxide and/or silicon nitride can be used as membrane materials. Particularly a liquid rubber, i.e. ELASTOSIL LR3003/10A, B can be used as a membrane material. The rubber membrane fulfills the stringent biocompatibility requirements necessary for medical applications, allows for relatively large pressures to be build up, e.g. when the substance is a solution which is pumped through the device, renders the sensor excellent thermal isolation properties, enables the active area to be very large and makes it possible to have optical access thanks to its transparency. Alternatively, instead of a membrane an insulating support plate, e.g. a glass plate or a polyvinylchloride (PVC-C) plate can be used.

To speed up measurement time or to test a number of substances at the same time, a modular system comprising an array of devices, each device comprising one thermopile, can be configured on the same substrate.

According to the present invention an example of a device (FIG. 1, b)) is disclosed based on only one thermopile (2) wherein said thermopile is in contact with a part of a substrate (1), e.g. a silicon wafer or the remains thereof. The cold junctions of said thermopile are coupled thermally to a first channel (3) comprising a first substance while the hot junctions of said thermopile are coupled thermally to a second channel (4) comprising a second substance, said first and said second channel are separated and thermally isolated one from another. The device further comprises a polyvinylchloride (PVC-C) support plate (6) at the bottom side and a similar plate (7) is used for ceiling the channels on the top side. The classical heat sink is omitted thereby fully exploiting the inherent benefits of a differential measurement using thermocouples as temperature sensing elements and resulting in a reduction in overall dimensions. Less area is consumed and the dead volume of the feeding fluid channels is reduced. Said device is capable of handling a very small amount of a substance, typically in the range from 1 microliter to 30 microliter. When used e.g. for drug screening, reference cells, forming a first substance, are adhered in the first channel, while in the second channel genetically engineered cells expressing a drug target are cultivated. When the potential drug candidate is effective, it will activate the genetically engineered cells, which form said second substance, and these will cause a heat change at one side of the thermopile, i.e. the hot junctions, thereby producing a differential voltage (heat conduction type calorimeter). The reference sample is thus substantially equal to the test sample except that it cannot produce a temperature change due to physiological activation. Consequently heat capacities and surface relationships are equal. The device as such has a very high common mode rejection ratio, offering a signal which is originating only from the potential drug candidate stimulating or suppressing the metabolism of the cells under study. To handle living cells and sticky reagents, materials where the device is composed of and which are in contact with said cells, need to be fully biocompatible and sterilisable.

According to the present invention an example of a method is disclosed for fabricating a device used to monitor chemical and physical processes which are accompanied by changes in heat content or enthalpy. The device is capable of handling a very small amount of a substance. These requirements can be achieved by micromachining, a technique closely related to integrated circuit fabrication technology. The starting material is a substrate like e.g. a semiconductive wafer, particularly a monocrystalline silicon wafer, or a slice of an insulating material, i.e. a glass slice. On this substrate layers can be coated, patterned by means of a sequence of lithographic steps and wet and/or dry etching steps. Such processed substrates can be bonded to each other or to other materials in order to make three-dimensional structures. A possible implementation of such a method or process is described below as an example without limiting the scope of the invention. The materials, dimensions and process steps mentioned in this example can be easily exchanged with equivalents or equivalent steps.

Figure 3:
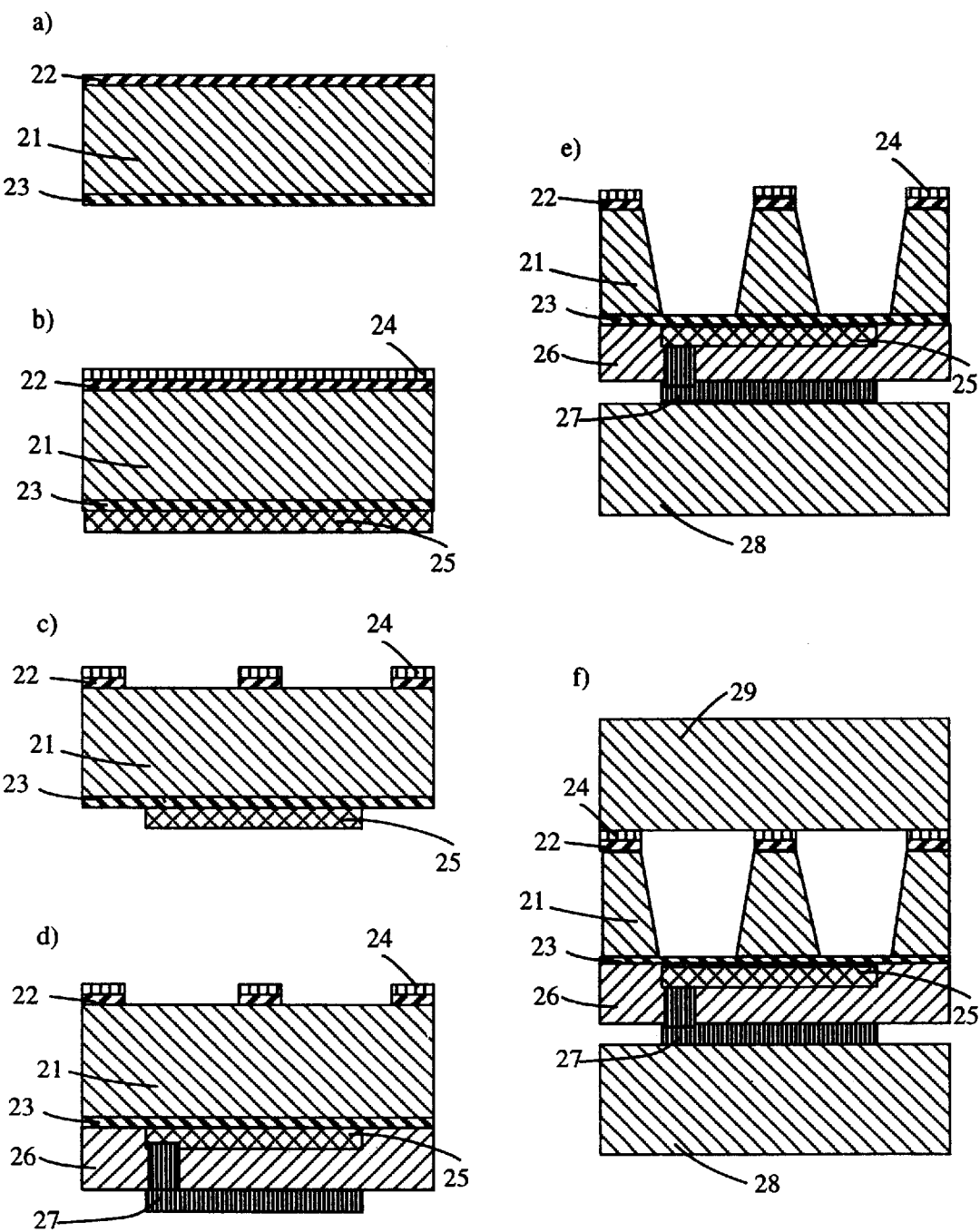
FIG. 3 depicts a schematic flow of a method for fabricating a thermal sensing device according to an embodiment of the present invention.

The process (FIG. 3) starts with the deposition of an oxide layer (FIG. 3, step a)) with a thickness of 470 nm on a first (22) and a second side (23) of a substrate (21), i.e. a monocrystalline silicon wafer. On the unpolished side, i.e. the first side, a nitride layer (24) with a thickness of 150 nm is deposited (FIG. 3, step b)) while on the other side, i.e. the second side, a first conductive layer (25), i.e. a p-type doped polysilicon layer with a thickness of about 1 $\mu$m is deposited. Said oxide layer on said second side of the substrate is provided as an etch stop layer for a back etch, as a layer which inhibits a direct contact of a substance to a thermopile and to thermally and electrically isolate said first conductive layer, being part of a thermopile.

On said first side of the substrate the nitride/oxide stack is patterned (FIG. 3, step c)) in order to define the etch windows for etching away the underlying silicon to form twin channels. Said channels are used to bring substances in close vicinity or in direct contact with the junctions of a thermopile. On said second side of the substrate the p-type doped polysilicon layer is patterned (FIG. 3, step c)) to thereby form the first material of the thermopile, i.e. a set of thermocouples which are connected in parallel thermally and in series electrically.

On said second side of the substrate an insulating layer (26) is deposited (FIG. 3, step d)) which is used as an interconductive layer dielectric and which isolates the different fingers of the polysilicon pattern. Said insulating layer is patterned to thereby form via holes through which the underlying polysilicon layer can be contacted in order to form hot junctions. A second conductive layer (27), having a thermo-electric voltage different from the thermo-electric voltage of said first conductive layer, i.e. an aluminum layer with a thickness of 200 nm, is deposited by means of evaporation on said second side of the substrate. Said second conductive layer is patterned to thereby form the second material of the thermopile. Aluminum and p-type polysilicon can be used to fabricate the thermopile because they are standard materials and their Seebeck coefficient is large. The dielectric layer between the conductive layers of the thermopile is a photosensitive resin derived from B-staged bisbenzocyclobutene (BCB) monomers.

The substrate is diced and said second side of the substrate is glued on a polyvinylchloride (PVC-C) support plate (28) before the back etch is done in KOH (FIG. 3, step e)). A similar plate (29) is used for ceiling (FIG. 3, step f)) the channels on the top side.

Instead of said support plate a membrane can be introduced in devices, which are used to monitor chemical and physical processes which are accompanied by changes in heat content or enthalpy and which comprise at least one thermopile, to thermally and electrically isolate said thermopile and to mechanically support said thermopile. When membranes larger than a few square centimeters need to be fabricated, conventional micromachining techniques have limitations. The materials where conventional membranes are composed of e.g. silicon oxide and/or silicon nitride. Due to residual stress in these silicon oxide and/or silicon nitride layer(s) which form the membrane, they easily bend, crack or even break. Therefore several polymers, particularly silicone rubber, have been investigated to make flexible large area membranes. The silicone rubber used is the two-component liquid silicone rubber ELASTOSIL LR3003/10A, B (Wacker Chemie). This rubber has a high mechanical strength, i.e. a tensile strength of about 2.5 MPa, a superior elongation at break of about 620%, a perfect biocompatibility, a low thermal conductivity of about 0.2 W/mK, a high electrical resistivity of about $5.10^{15}$ $\Omega$cm, a low water uptake, a high gas permeability and a relatively low viscosity. The latter property makes a spincoating technique feasible.

The biocompatibility, high mechanical strength, high degree of transparency and low thermal conductivity of this silicone rubber invite to many application domains where conventional micromachining techniques fail. This silicone rubber can be introduced as a membrane in sensing devices comprising a thermopile. Transferring a thermopile to a rubber membrane renders excellent thermal isolation properties to the thermopile as the thermal conductance of the rubber is very small (0.2 W/mK) and the membrane can be made very thin ($\mu$m range). Moreover, it offers the possibility to prepare a large size thermopile which is needed if good thermal isolation and high sensitivity are desired. Large areas are also needed if the metabolism of biological cells is being tested as cells are preferably tested in monolayers and a large number of them are needed to get a significant signal (power production of a single cell is in the order of picoWatts). Furthermore the rubber membrane fulfills the stringent biocompatibility requirements, which makes it suited for medical applications, and can sustain relatively large pressures. The use of this silicone rubber is not limited to its function as a membrane in sensing devices comprising a thermopile. Due the its high thermal resistivity this rubber can be used to thermally isolate at least parts of all kind of sensing devices. Due to its mechanical strength and elasticity this rubber can be used in all kind of sensing devices which benefit from these properties like e.g. flow sensing devices and actuators. Due to its low viscosity this rubber can be introduced in sensing devices by means of a spin coating technique for protection, sealing and packaging purposes. Furthermore, the transparency of the rubber opens the field for applications where optical access is needed, e.g. microscopic analyzing techniques.

Figure 4:
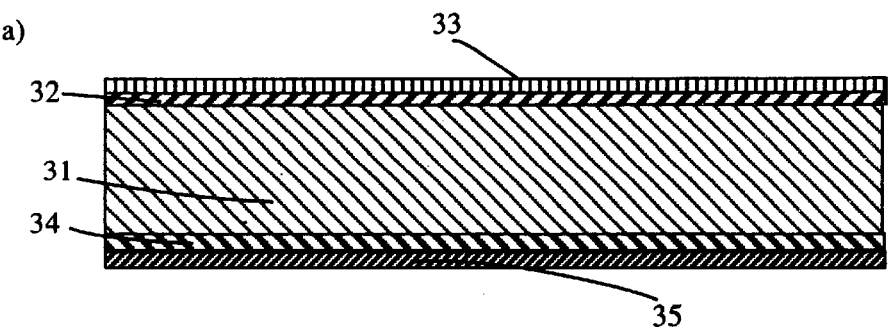
FIG. 4 depicts a schematic flow of a method for fabricating a rubber membrane, i.e. a membrane composed of ELASTOSIL LR3003/10A, B (Wacker Chemie), according to an embodiment of the invention.
Figure 4:
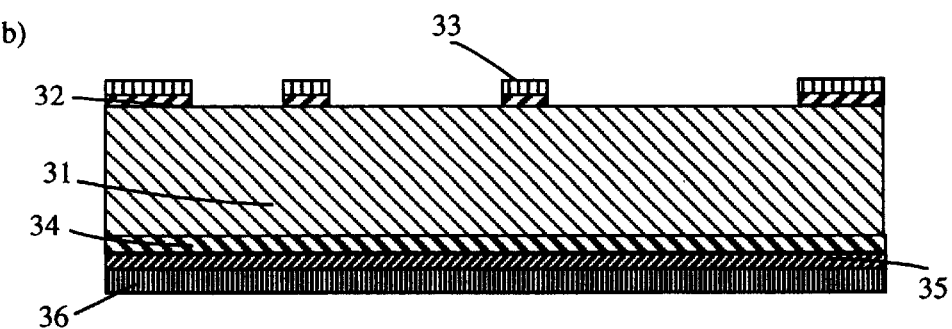
Figure 4:
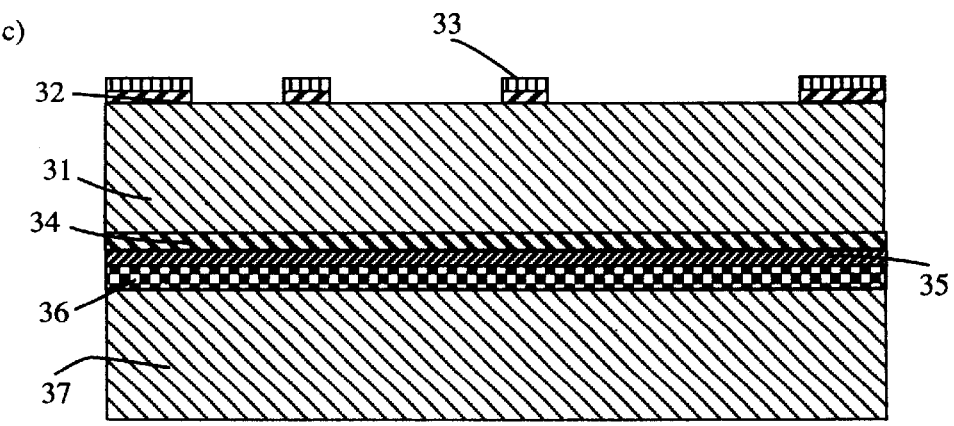
Figure 4:
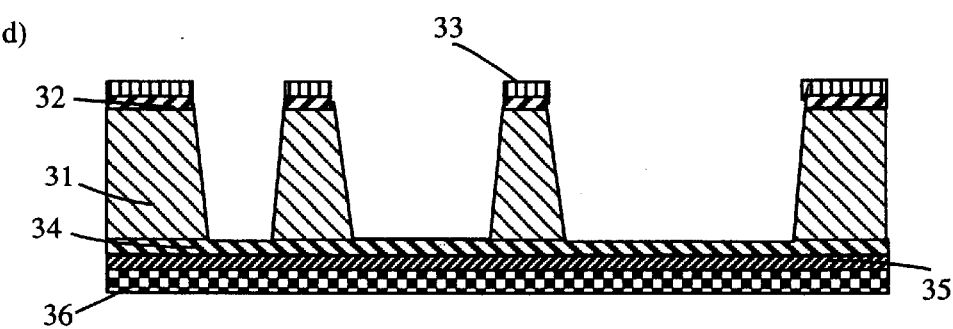

In an embodiment of the invention a method (FIG. 4) is disclosed for fabricating rubber membranes. This method comprises the following steps:

On a first side of a substrate (31) a silicon oxide/silicon nitride stack is deposited (FIG. 4, step a)) which will serve as an etch mask to define the membrane pattern. The oxide layer (32) has a thickness of 470 nm, while the thickness of the nitride layer (33) is 150 nm. Other materials and/or other thickness and or another number of layers may be used to serve as an etch mask. When using an oxide/nitride stack, preferably the ratio of the thickness of the oxide and the nitride layer is about three to balance out the tensile and compressive forces. Said substrate can be a semiconductive wafer or slice, like e.g. a silicon wafer, or an insulating slice like e.g. a glass slice. Particularly, a six inch p-type (100) oriented monocrystalline silicon wafer is used.

On the second side of the substrate a silicon oxide/silicon nitride stack is deposited which will serve as an etch stop to define the membrane pattern. The oxide layer (34) has a thickness of 470 nm while the thickness of the nitride layer (35) is 150 nm. Other, preferably insulating, materials and/or other thickness and or another number of layers may be used to serve as an etch stop. When using an oxide/nitride stack, preferably the ratio of the thickness of the oxide and the nitride layer is about three to balance out the tensile and compressive forces. One can also choose to omit this etch stop dependent on the etch procedure.

The oxide/nitride stack on said first side of the substrate is patterned (FIG. 4, step b)) by means of a sequence of photolithographic steps and wet and/or dry etching steps.

The second side of the substrate is coated with liquid rubber, i.e. ELASTOSIL LR3003/10A, B (Wacker Chemie) (36). The relatively low viscosity of said rubber allows for a spin-coating technique. By varying the speed and the time of spinning, the thickness of the layer can be adjusted ranging from 5 to 50 $\mu$m. For larger thickness, a multilayer structure can be fabricated by spinning different layers on top of each other. A spinrate of 3000 rpm and a spintime of 60 seconds renders a layer thickness of about 70 $\mu$m. The surface of the substrate is chemically modified to make it water repellent by treating said surface with hexamethyldisiloxane (HMDS). The viscosity of the rubber, and thus the layer thickness, can be reduced by adding small amounts of silicone oil.

A second substrate (37), particularly a second 6 inch wafer is bonded (FIG. 4, step c)) onto the first by means of the unvulcanised rubber. The bonding is performed in low vacuum to avoid air bubble formation at the substrate-rubber interface. To cure the rubber, the structure is baked for 3 minutes at 170° C. on a hot plate. Alternatively, in stead of a second wafer a glass plate is used. A first side of this glass plate comprises a wax layer to protect the rubber layer of the first substrate because said first side is exposed to the rubber during the bonding process.

To form the membrane a chemical back etch (FIG. 4, step d)) is performed in 35 w % KOH at 60° C. The last 10 $\mu$m of silicon is etched at room temperature to minimize the risk of breaking the oxide/nitride layer underneath. The rubber type used is not attacked by KOH at room temperature so the second sacrificial substrate needs no etch stop. If the bottom oxide/nitride layer of the first substrate is not a structural element of the design, it be omitted from the beginning, making the rubber layer an etch stop for both etching sides. The oxide/nitride stack is necessary in cases where e.g. gas impermeability is needed (the rubber is permeable for gasses) or chemicals need to be transported which attack the rubber. In case a waxed glass plate is used instead of a silicon wafer, the second side of said plate is etched in KOH at 40° C. The wax is removed by 1,1,1-trichloroethane.

Figure 5:
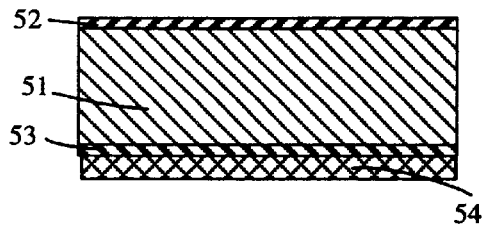
FIG. 5 depicts a schematic flow of a method for fabricating a thermal sensing device according to an embodiment of the present invention.
Figure 5:
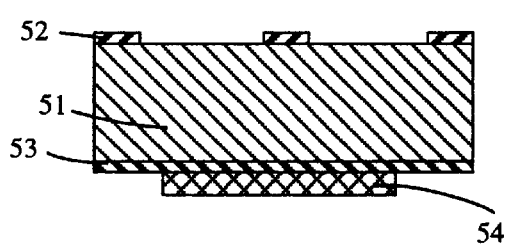
Figure 5:
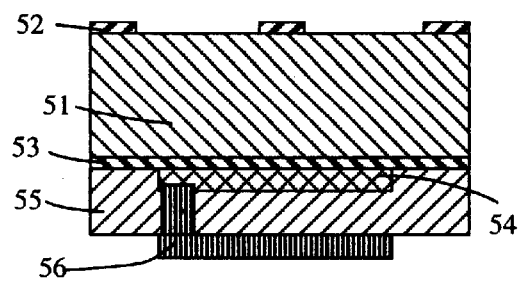
Figure 5:
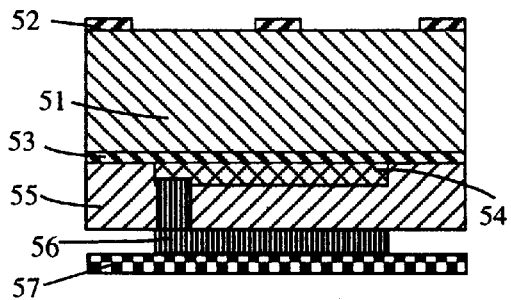
Figure 5:
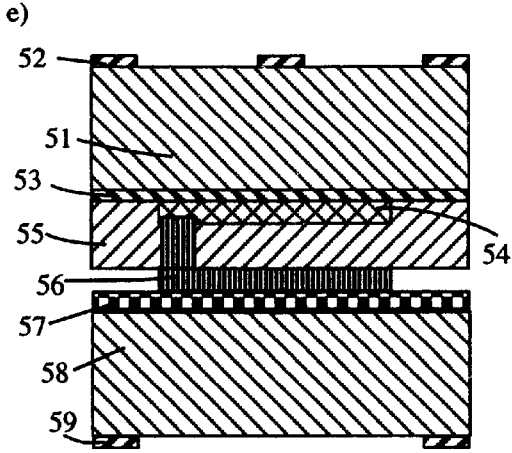
Figure 5:
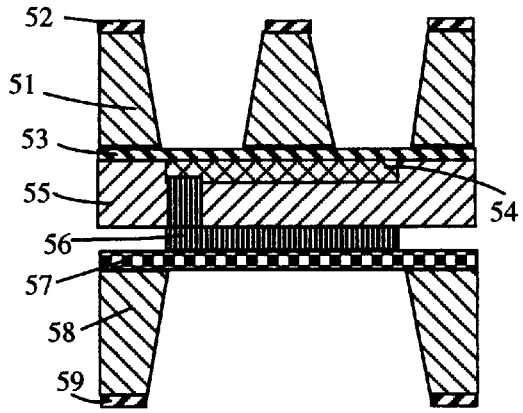

In an embodiment of the invention a method is disclosed for fabricating a device used to monitor chemical and physical processes which are accompanied by changes in heat content or enthalpy. The device can be capable of handling a very small amount of a substance. These requirements can be achieved by micromachining, a technique closely related to integrated circuit fabrication technology. The starting material is a substrate like e.g. a semiconductive wafer or slice, particularly a monocrystalline silicon wafer, or a slice or plate of an insulating material, i.e. a glass slice. Particularly a 150 mm silicon wafer is chosen. This method or process comprises the following steps (FIG. 5):

On a first side of a substrate (51) at least one hard mask layer (52) is deposited (FIG. 5, step a)) which will serve as an etch mask for removing at least parts of said substrate. An example of said hard mask layer is a multi-layer structure comprising a first layer e.g. silicon oxide and a second layer e.g. a silicon nitride. Other materials and/or another number of layers may be chosen dependent on their suitability as an etch mask. When choosing for an oxide/nitride stack, preferably the ratio of the thickness of the oxide and the nitride layer is about three to balance out the tensile and compressive forces. This results in an oxide layer with a thickness which is typically about 450 nm while the thickness of the nitride layer is typically about 150 nm.

On the second side of the substrate at least one insulating layer (53) can be deposited which can serve as an etch stop layer dependent on the etch procedure used and/or as an insulating layer to thermally and electrically isolate a thermopile and/or to inhibit a direct contact between a substance and said thermopile. An example of said hard mask layer is a multi-layer structure comprising a first layer e.g. a silicon oxide layer and a second layer e.g. a silicon nitride layer. Other insulating materials and/or another number of layers may be chosen dependent on their suitability as an etch stop. When choosing for an oxide/nitride stack, preferably the ratio of the thickness-of the oxide and the nitride layer is about three to balance out the tensile and compressive forces. This results in an oxide layer with a thickness which is typically about 450 nm while the thickness of the nitride layer is typically about 150 nm. One can also choose to omit at least a part of this multi-layer structure when its only function is to provide an etch stop, dependent on the etch procedure used.

On said second side of the substrate a first conductive layer (54) with a thickness typically in the range from 0.3 $\mu$m to 1 $\mu$m is deposited. The choice of said conductive layer is based on several parameters as there are the magnitude of its Seebeck coefficient, the electrical resistivity, its availability and the compatibility with standard processing steps as used in the manufacturing of integrated circuits. An increase in Seebeck coefficient corresponds with an increase in sensitivity while a lower resistivity corresponds with a lower noise level and thus an improved signal to noise ratio. The resistance of said conductive layer is of course not only determined by its resistivity but also its dimensions which is at least partly a design issue. An example of such a conductive layer is a doped polysilicon layer. In case a polysilicon layer is chosen, said layer is doped after deposition.

On said first side of the substrate the nitride/oxide stack is patterned (FIG. 5, step b)) in order to define the etch windows for etching away the underlying silicon in order to expose at least parts of the underlying thermopile or the etch stop multilayer structure on said thermopile. This can be done to form channel regions in the vicinity of the thermopile junctions. These channel regions can be used to bring a test or reference substance in contact or in the vicinity of the junctions of said thermopile. These channel regions can also be used as molds for fitting in e.g. glass tubes, where said glass tubes are used to bring a test or a reference substance in the vicinity of said thermopile thereby avoiding a direct contact between said substance and said thermopile. Alternatively, in stead of etching channel regions, one can also choose to expose the underlying thermopile or the etch stop multi-layer structure on said thermopile as a whole. In the latter case the reference substance or the test substance is applied directly on said thermopile.

On said second side of the substrate said first conductive layer (54), e.g. a doped polysilicon layer is patterned to thereby form the first material of the thermopile, i.e. a set of thermocouples which are preferably connected in parallel thermally and in series electrically.

On said second side of the substrate an insulating layer (55) is deposited (FIG. 5, step c)) with a thickness in the range typically from 0.2 $\mu$m to 1 $\mu$m or from 0.5 $\mu$m to 5 $\mu$m. Said insulating layer is used as an interconductive layer dielectric and isolates the different fingers of the polysilicon pattern from each other. Said insulating layer is patterned to thereby form via holes through which the underlying first conductive layer can be contacted in order to form hot junctions. Examples of such insulating layers are a silicon oxide layer and a benzocyclobutene (BCB) layer.

A second conductive layer (56), having a thermo-electric voltage different from the thermo-electric voltage of said first conductive layer, i.e. an aluminum layer with a thickness of 200 nm, is deposited e.g. by means of evaporation on said second side of the substrate. Said second conductive layer is patterned to thereby form the second material of the thermopile.

On said second side of the substrate an insulating layer (57) is deposited (FIG. 5, step d)) to serve as a membrane. Said membrane should thermally and electrically isolate said thermopile and mechanically support said thermopile. Silicon oxide and/or silicon nitride can be used as membrane materials, but preferably a liquid rubber, i.e. ELASTOSIL LR3003/10A, B (Wacker Chemie) is used. The rubber membrane fulfills the stringent biocompatibility requirements necessary for medical applications, allows for relatively large pressures to be build up, e.g. when the test substance is a solution which is pumped through the device, renders the sensor excellent thermal isolation properties, enables the active area to be very large and makes it possible to have optical access thanks to its transparency. The relatively low viscosity of said rubber allows for a spin-coating technique. By varying the speed and the time of spinning, the thickness of the layer can be adjusted ranging from 5 to 50 $\mu$m. For larger thickness, a multilayer structure can be fabricated by spinning different layers on top of each other. A spinrate of 3000 rpm and a spintime of 60 seconds renders a layer thickness of about 70 $\mu$m. The surface of the substrate is chemically modified to make it water repellent by treating said surface with hexamethyldisiloxane (HMDS). The viscosity of the rubber, and thus the layer thickness, can be further reduced by adding small amounts of silicone oil resulting in layer thickness down to 1 $\mu$m.

A second substrate (58), particularly a second 150 mm silicon wafer, is bonded (FIG. 5, step e)) onto said first substrate by means of the unvulcanised rubber. The bonding is performed in low vacuum to avoid air bubble formation at the substrate-rubber interface. To cure the rubber, the structure is baked for 3 minutes at 170° C. on a hot plate. Alternatively, in stead of a second wafer a glass plate is used. A first side of this glass plate comprises a wax layer to protect the rubber layer of the first substrate because said first side is exposed to the rubber during the bonding process.

To expose the thermopile and the membrane, a chemical back etch is performed (FIG. 5, step f)) in 35 w % KOH at 60° C. The last 10 $\mu$m of silicon is etched at room temperature to minimize the risk of breaking the oxide/nitride layer on said thermopile. The rubber type used is not attacked by KOH at room temperature so the second sacrificial substrate needs no etch stop. In case a waxed glass plate is used in stead of a silicon wafer, the second side of said plate is etched in KOH at 40° C. The wax is removed by 1,1,1-trichloroethane. Alternatively an etch mask (59), e.g. a silicon oxide/silicon nitride stack, can be deposited and patterned on the free surface of said second substrate. By doing so, during the back etch e.g. only the glass or silicon underneath the thermopile is removed to thereby free the membrane.

Alternatively, instead of forming a membrane on said thermopile one can also choose to fix a substrate, like e.g. a glass plate or a polyvinylchloride plate, directly on said thermopile. Said substrate will isolate and mechanically support said thermopile.

What is claimed is:

1. A device for monitoring processes which are accompanied by changes in heat content or enthalpy comprising:
   a substrate, said substrate having at least one opening;
   a membrane having a first surface and a second surface, said membrane mechanically supported by said substrate on at least one point on said second surface and spanning at least a part of said opening;
   a thermopile with a cold junction located in a first region on said first surface of said membrane, and a hot junction located in a second region on said first surface of said membrane, said first region and said second region being positioned opposite said opening; said membrane thermally and electrically isolating said first and second regions; and,
   a first supply for bringing a first substance in thermal contact with said first region and a second supply for bringing a second substance in thermal contact with said second region, wherein said first substance is separated and thermally isolated from said second substance.

2. A device as recited in claim 1 further wherein said substrate is selected from a group comprising:
   silicon wafers, silicon slices, glass slices, glass plates, polymers and plastics.

3. A device as recited in claim 2 further comprising a protective layer on said thermopile.

4. A device as recited in claim 1 wherein said membrane is further selected from a group comprising oxides and nitrides.

5. A device for monitoring processes which are accompanied by changes in heat content or enthalpy, comprising:
   a lower substrate having at least opening;
   a membrane with a first surface and a second surface, said second surface of said membrane being supported by said substrate on at least one point and spanning at least a part of said opening; and
   a thermopile having a cold junction located in a first region on said first surface of said membrane and a hot junction located in a second region on said first surface of said membrane, said first region and said second region being positioned above said opening, wherein said first region and said second region are thermally isolated.

6. A device for monitoring processes which are accompanied by changes in heat content or enthalpy comprising:
   a substrate having at least two openings;

a membrane having a first surface and a second surface, said membrane mechanically supported by said substrate on at least one point on said second surface and spanning at least a part of said at least two openings;

a thermopile with a cold junction located in a first region on said first surface of said membrane, and a hot junction located in a second region on said first surface of said membrane, said first region being positioned above a first opening and said second region being positioned above a second opening; said membrane thermally and electrically isolating said first and second regions.

* * * * *